(12) United States Patent
Alvarez et al.

(10) Patent No.: US 11,246,973 B2
(45) Date of Patent: Feb. 15, 2022

(54) THERMAL SYSTEM WITH DRAINAGE BAG

(71) Applicant: Stryker Corporation, Kalamazoo, MI (US)

(72) Inventors: Ryan Ariel Alvarez, Kalamazoo, MI (US); Venkata Ravi Varma Mudunuri, Kalamazoo, MI (US); Teresa Lynn Miller, Plainwell, MI (US); Jack Louis Leckner, South Lyon, MI (US); Alexey Titov, Redmond, WA (US)

(73) Assignee: Stryker Corporation, Kalamazoo, MI (US)

( * ) Notice: Subject to any disclaimer, the term of this patent is extended or adjusted under 35 U.S.C. 154(b) by 413 days.

(21) Appl. No.: 16/263,061

(22) Filed: Jan. 31, 2019

(65) Prior Publication Data

US 2019/0231938 A1 Aug. 1, 2019

Related U.S. Application Data

(60) Provisional application No. 62/626,826, filed on Feb. 6, 2018, provisional application No. 62/624,581, filed on Jan. 31, 2018.

(51) Int. Cl.
*A61M 1/00* (2006.01)
*A61J 1/10* (2006.01)
(Continued)

(52) U.S. Cl.
CPC ............ *A61M 1/69* (2021.05); *A61F 7/00* (2013.01); *A61J 1/10* (2013.01); *A61J 1/1475* (2013.01);
(Continued)

(58) Field of Classification Search
CPC .. A61M 1/69; A61J 1/10; A61J 1/1475; A61J 1/1462; A61L 2300/602
See application file for complete search history.

(56) References Cited

U.S. PATENT DOCUMENTS

| | | | | |
|---|---|---|---|---|
| 4,363,406 A | * | 12/1982 | Salvadori | A61M 1/69 383/200 |
| 6,183,461 B1 | * | 2/2001 | Matsuura | A61M 31/002 604/502 |

(Continued)

FOREIGN PATENT DOCUMENTS

WO WO 2018/007691 * 1/2018

*Primary Examiner* — Ariana Zimbouski
(74) *Attorney, Agent, or Firm* — Warner Norcross + Judd LLP

(57) ABSTRACT

A drainage bag is provided for a thermal control unit adapted to deliver temperature-controlled liquid to a patient in order to control the patient's temperature. The drainage bag is used to hold and transport the liquid when the liquid inside the thermal control unit is changed. The drainage bag includes a bottom layer, a top layer sealed thereto, and a float secured to the top layer that is positioned adjacent an opening in the top layer. As the liquid from the thermal control unit drains into the opening in the top layer, the liquid lifts the float and the float lifts the top layer of the bag. The bag thereby expands its volume to accommodate the liquid from the thermal control unit. The bag may further be designed to be carried without sealing the opening and without spilling the liquid. A method for using the bag is also disclosed.

11 Claims, 12 Drawing Sheets

(51) Int. Cl.
 *A61J 1/14* (2006.01)
 *A61F 7/00* (2006.01)
 *A61M 5/44* (2006.01)

(52) U.S. Cl.
 CPC .............. *A61M 5/44* (2013.01); *A61J 1/1462* (2013.01); *A61L 2300/602* (2013.01); *A61M 2205/36* (2013.01)

(56) References Cited

U.S. PATENT DOCUMENTS

| | | | |
|---|---|---|---|
| 7,731,739 B2 * | 6/2010 | Schock | A61F 7/00 607/107 |
| 2010/0130949 A1 * | 5/2010 | Garcia | A61M 1/0023 604/326 |
| 2010/0228196 A1 * | 9/2010 | Wyss | A61M 5/148 604/151 |

* cited by examiner

THERMAL SYSTEM WITH DRAINAGE BAG

CROSS-REFERENCE TO RELATED APPLICATIONS

This application claims priority to U.S. provisional patent application Ser. No. 62/624,581 filed Jan. 31, 2018, by inventors Ryan Ariel Alvarez et al. and entitled THERMAL SYSTEM WITH DRAINAGE BAG, as well as U.S. provisional patent application Ser. No. 62/626,826 filed Feb. 6, 2018, by inventors Ryan Ariel Alvarez et al. and entitled THERMAL SYSTEM WITH DRAINAGE BAG, the complete disclosures of both of which are incorporated herein by reference.

BACKGROUND

The present disclosure relates to a thermal control system for controlling the temperature of circulating fluid that is delivered to one or more thermal pads positioned in contact with a patient, and more particularly to a drainage bag for draining the liquid from the thermal control system.

Thermal control systems are known in the art for controlling the temperature of a patient by providing a thermal control unit that supplies temperature-controlled fluid to one or more thermal pads positioned in contact with a patient and/or to one or more catheters positioned inside the patient. The thermal control unit includes one or more heat exchangers for controlling the temperature of the fluid and a pump that pumps the temperature-controlled fluid to the pad(s) and/or catheter(s). After passing through the pad(s) or catheter(s), the fluid is returned to the thermal control unit where any necessary adjustments to the temperature of the returning fluid are made before being pumped back to the pad(s) and/or catheter(s).

Periodically, it is often desirable to change the liquid inside the thermal control unit, which is typically water, or a water-based mixture (although other liquids may be used). In order to drain the liquid from the thermal control unit, a valve on the thermal control unit is typically opened to allow the liquid to drain out of the thermal control unit due to gravity. After the liquid is drained, the valve is closed and a disinfected and/or fresh supply of liquid is added back to the thermal control unit. In some instances, draining the thermal control unit without spilling the liquid onto the floor and/or other surfaces is difficult.

SUMMARY

The present disclosure provides a drainage bag and method of using the drainage bag that facilitate the emptying of the thermal control unit with relative ease and less chance of spillage. In some embodiments, the drainage bag is a substantially flat structure that can be compactly stored and that automatically expands its volume when liquid is initially drained into the bag to thereby receive the liquid without spillage. The bag may be made of flexible plastic material or other items that are relatively inexpensive, thereby allowing the drainage bag to be disposed of after use, if desired.

According to one embodiment of the present disclosure, a drainage bag is provided for use with a thermal control unit adapted to deliver temperature-controlled liquid to a patient in order to control a temperature of a patient. The drainage bag comprises a bottom layer, a top layer, an opening, and a float. The top layer is positioned on top of the bottom layer and sealed to the bottom layer about a perimeter. The top layer and bottom layer define an interior space therebetween that lies within the perimeter. The opening is defined in the top layer and the float is adapted to lift a region of the top layer adjacent the opening as liquid from the thermal control unit is drained into the interior space from above the top and bottom layers.

According to other aspects of the present disclosure, the top layer is made of a flexible plastic and adapted to rest on top of the bottom layer when the interior space is empty of liquid. The bottom layer may also be made of a flexible plastic which, in some instances, is the same material as the top layer.

The float is constructed of a material that is buoyant in the particular liquid used with the thermal control unit. In some embodiments, the float includes at least one air pocket hermetically isolated from the interior space. The air pocket may be defined in the same material used to construct the top layer, such as a flexible plastic.

In some embodiments, the float includes a plurality of air pockets hermetically isolated from the interior space and the plurality of air pockets are distributed over and coupled to the top layer.

The drainage bag is dimensioned in at least one embodiment to hold a volume of liquid that is greater than or equal to a maximum liquid capacity of the thermal control unit. In such embodiments, the float is adapted to lift the top layer above the bottom layer such that a volume of the interior space expands sufficiently to receive the full maximum liquid capacity of the thermal control unit in the interior space without the liquid spilling out of the interior space through the opening.

In some embodiments, the opening is defined in the top layer at a position offset from a center of the perimeter.

At least one handle is included in some embodiments. The handle is coupled to the top and bottom layers and is adapted to allow a user to pull the drainage bag out from a generally horizontal orientation underneath the thermal control unit and to allow the user to lift the drainage bag to a generally vertical orientation.

In some embodiments, the opening is defined in the top layer at a position such that, when the drainage bag is lifted to the generally vertical orientation, the portion of the interior space that is located below the opening has a volume greater than or equal to the maximum volume of liquid.

In some embodiments, the opening remains open when the drainage bag is lifted to the generally vertical orientation, while in other embodiments, a valve or seal may be included to close the opening.

The top and bottom layers, in some embodiments, are both substantially planar and in contact with each other when the interior space is empty of liquid. This gives the interior space a volume that substantially equal to zero, thereby allowing the bag to occupy very little space when not in use.

According to another embodiment of the present disclosure, a method of draining liquid from a thermal control unit is provided. The thermal control unit is adapted to deliver temperature-controlled liquid to a patient in order to control a temperature of a patient, and the method comprises: providing a drainage bag having a flexible top layer coupled to a bottom layer, a float coupled to the top layer, and an interior space defined between the top layer and bottom layer that has a volume that varies with flexing of the top layer away from the bottom layer; positioning the drainage bag underneath the thermal control unit such the bottom layer lies on a surface and faces away from the thermal control unit and the top surface faces toward a bottom of the thermal control unit; aligning an opening in the top layer with a drainage port positioned on the bottom of the thermal control unit; opening the drainage port to allow liquid within the thermal control unit to drain out of the thermal control unit through the drainage port and into the opening; and allowing the float to lift the top layer as the liquid enters the opening such that the volume of the interior space expands sufficiently to receive the liquid from the drainage port.

According to other aspects of the present disclosure, the method may further include pulling the drainage bag out from under the thermal control unit via a handle of the drainage bag.

In some embodiments, the method also includes lifting the drainage bag into a generally vertical orientation via the handle, wherein the opening is positioned higher than a level of liquid within the interior space when the bag is in the generally vertical orientation.

The method may further include allowing the top layer to rest on the bottom layer when positioning the drainage bag underneath the thermal control unit prior to opening the drainage port.

When pulling the drainage bag out from under the thermal control unit, the method may include pulling the drainage bag without sealing the opening, lifting the drainage bag without sealing the opening, and transporting the drainage bag to a drain for disposing of the liquid without sealing the opening.

In some embodiments, the method includes allowing the float to lift the top layer until the volume of the interior space expands sufficiently to receive substantially all of the liquid within the thermal control unit.

The method may also or alternatively include laying the bottom layer substantially flat on the surface underneath the thermal control.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
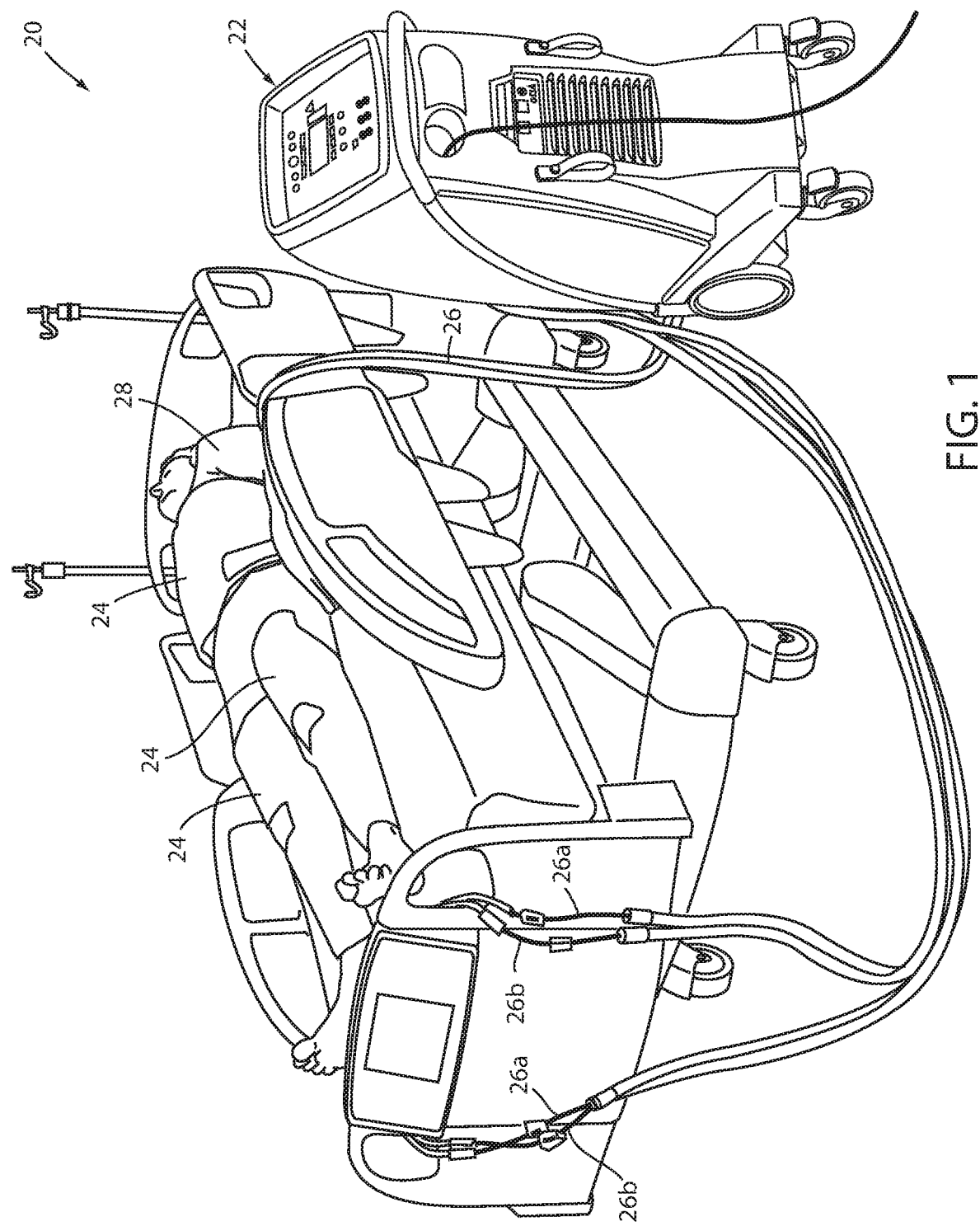
FIG. 1 is a perspective view of an illustrative thermal control system with which the drainage bag of the present disclosure may be used.

An example of a thermal control system 20 with which drainage bags of the present disclosure may be used is shown in FIG. 1. It will be understood that thermal control system 20 is merely one illustrative example of the type of thermal control systems with which the drainage bags disclosed herein may be used. The details and/or construction of thermal control system 20 described herein are therefore merely illustrative examples that are not intended to limit the thermal control systems in which the drainage bags may be used.

Thermal control systems of the type shown in FIG. 1 are adapted to raise, lower, and/or maintain a patient at a desired temperature. Such thermal control systems include a thermal control unit, such as thermal control unit 22, which is coupled to one or more thermal therapy devices 24. The thermal therapy devices 24 illustrated in FIG. 1 are shown as thermal pads, but it will be understood that thermal therapy devices 24 may take on other forms, such as, but not limited to, blankets, vests, patches, caps, catheters, or other structures that receive temperature-controlled fluid. For purposes of the following written description, thermal therapy devices 24 will be referred to as thermal pads 24, but it will be understood by those skilled in the art that this terminology is used merely for convenience and that the phrase "thermal pad" is intended to cover all of the different variations of thermal therapy devices 24 mentioned above (e.g. blankets, vests, patches, caps, catheters, etc.).

Thermal control unit 22 is coupled to thermal pads 24 via a plurality of hoses 26. Thermal control unit 22 delivers temperature-controlled fluid (such as, but not limited to, water or a water mixture) to the thermal pads 24 via the fluid supply hoses 26a. After the temperature-controlled fluid has passed through thermal pads 24, thermal control unit 22 receives the temperature-controlled fluid back from thermal pads 24 via the return hoses 26b.

In the embodiment of thermal control system 20 shown in FIG. 1, three thermal pads 24 are used in the treatment of patient 28. A first thermal pad 24 is wrapped around a patient's torso, while second and third thermal pads 24 are wrapped, respectively, around the patient's right and left legs. Other configurations can be used and different numbers of thermal pads 24 may be used with thermal control unit 22, depending upon the number of inlet and outlet ports that are included with thermal control unit 22. By controlling the temperature of the fluid delivered to thermal pads 24 via supply hoses 26a, the temperature of the patient 28 can be controlled via the close contact of the pads 24 with the patient 28 and the resultant heat transfer therebetween.

Thermal control unit 22 is adapted to raise or lower the temperature of the fluid supplied to thermal pads 24. In order to do so, thermal control unit 22 includes one or more pumps, heaters, chillers, temperature sensors, and/or other components necessary to supply temperature-controlled fluid to the thermal pads 24. In many thermal control systems, the liquid supplied to the thermal pads 24 is water, or a water-based solution, although it will be understood that other types of liquid may be used with a particular thermal control system, and that the drainage bags disclosed herein may be used for draining any type of liquid used with thermal control systems 20. Further details about the operation and construction of one example of thermal control unit 22 may be found in, for example, commonly assigned U.S. patent application Ser. No. 14/282,383 filed May 20, 2014, by inventors Christopher Hopper et al. and entitled THERMAL CONTROL SYSTEM, the complete disclosure of which is incorporated herein by reference. As noted, the particular details of thermal control system 20 may vary widely and the drainage bags discussed herein may be used with any type of thermal control system that utilizes a liquid that, at some point in time, is drained from the thermal control unit.

Figure 2:
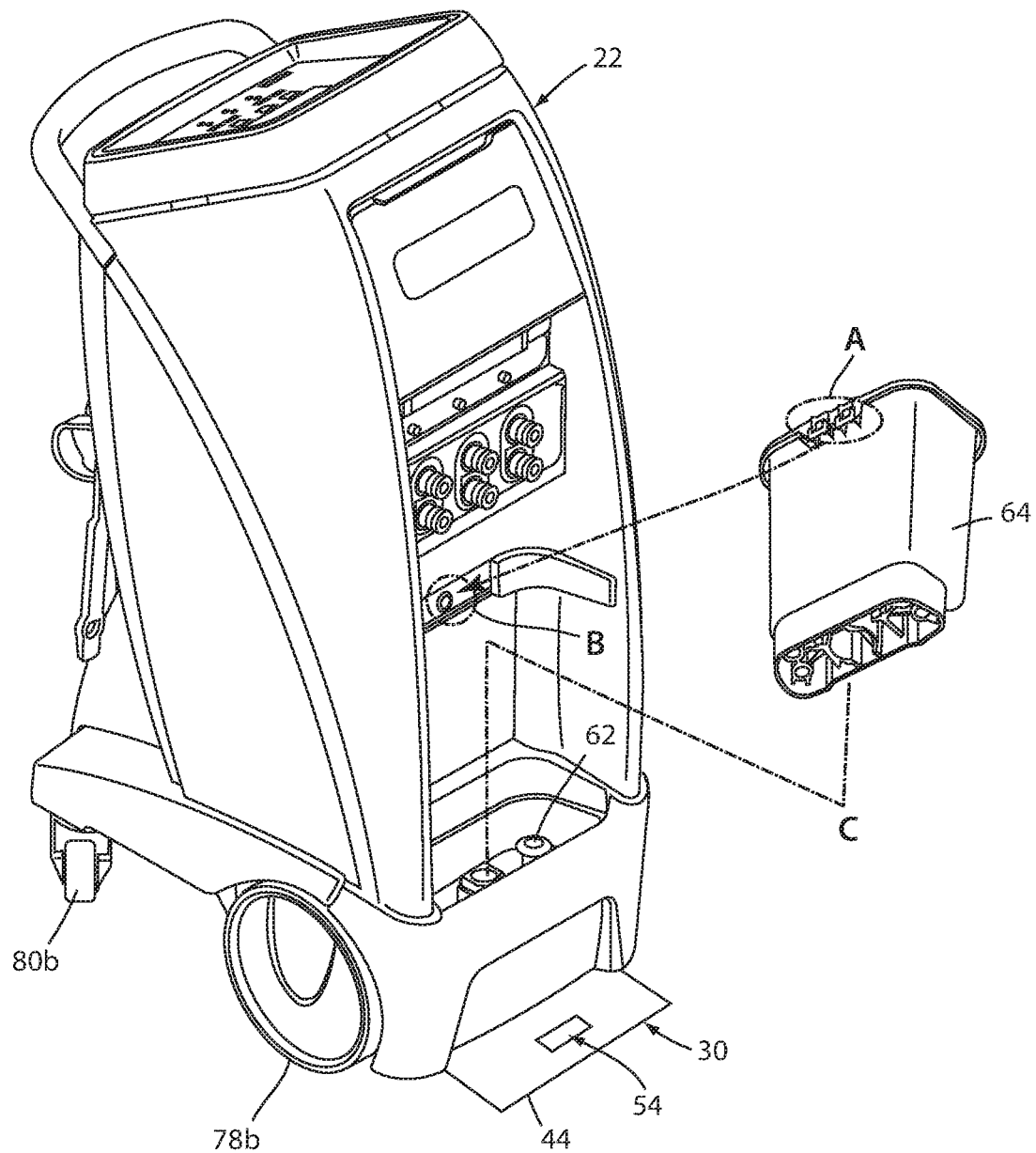
FIG. 2 is a perspective view of the thermal control unit of the thermal control system of FIG. 1 shown with a drainage bag according to a first embodiment of the present disclosure positioned underneath.

FIG. 2 illustrates one embodiment of a drainage bag 30 according to the present disclosure. Drainage bag 30 is shown in FIG. 2 in a position underneath thermal control unit 22 where it is configured to receive and hold the liquid that is drained from thermal control unit 22. Thermal control unit 22 is configured to drain its liquid from a drainage port (discussed more below) that is located underneath the unit. Drainage bag 30 is designed to be placed underneath the drainage port and receive the liquid as it drains. Once the liquid has drained, the drainage bag may be pulled out from underneath thermal control unit 22, lifted, and carried to a sink or other location where the liquid may be disposed of. Further details regarding the construction of drainage bag 30 and the methods of using drainage bag 30 will now be provided.

Figure 3:
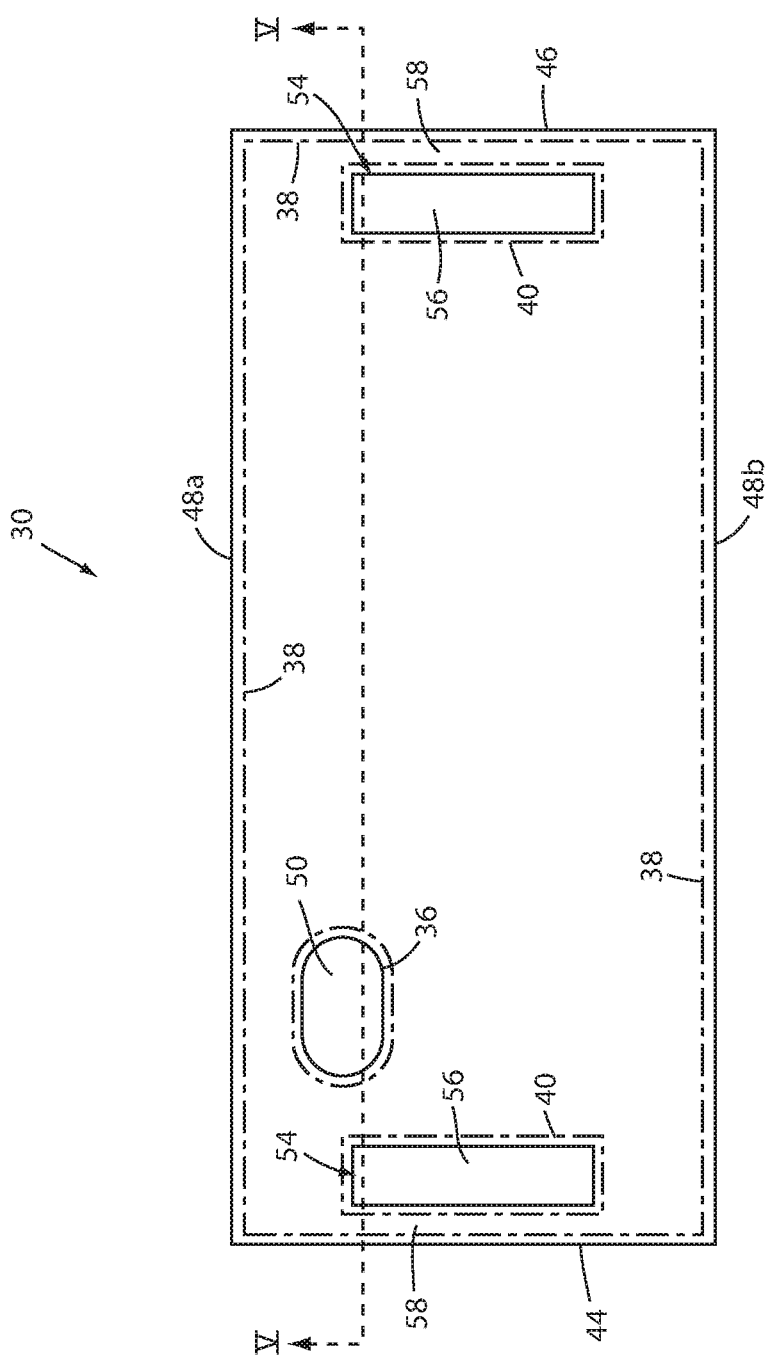
FIG. 3 is a plan view of the drainage bag of FIG. 2.
Figure 4:
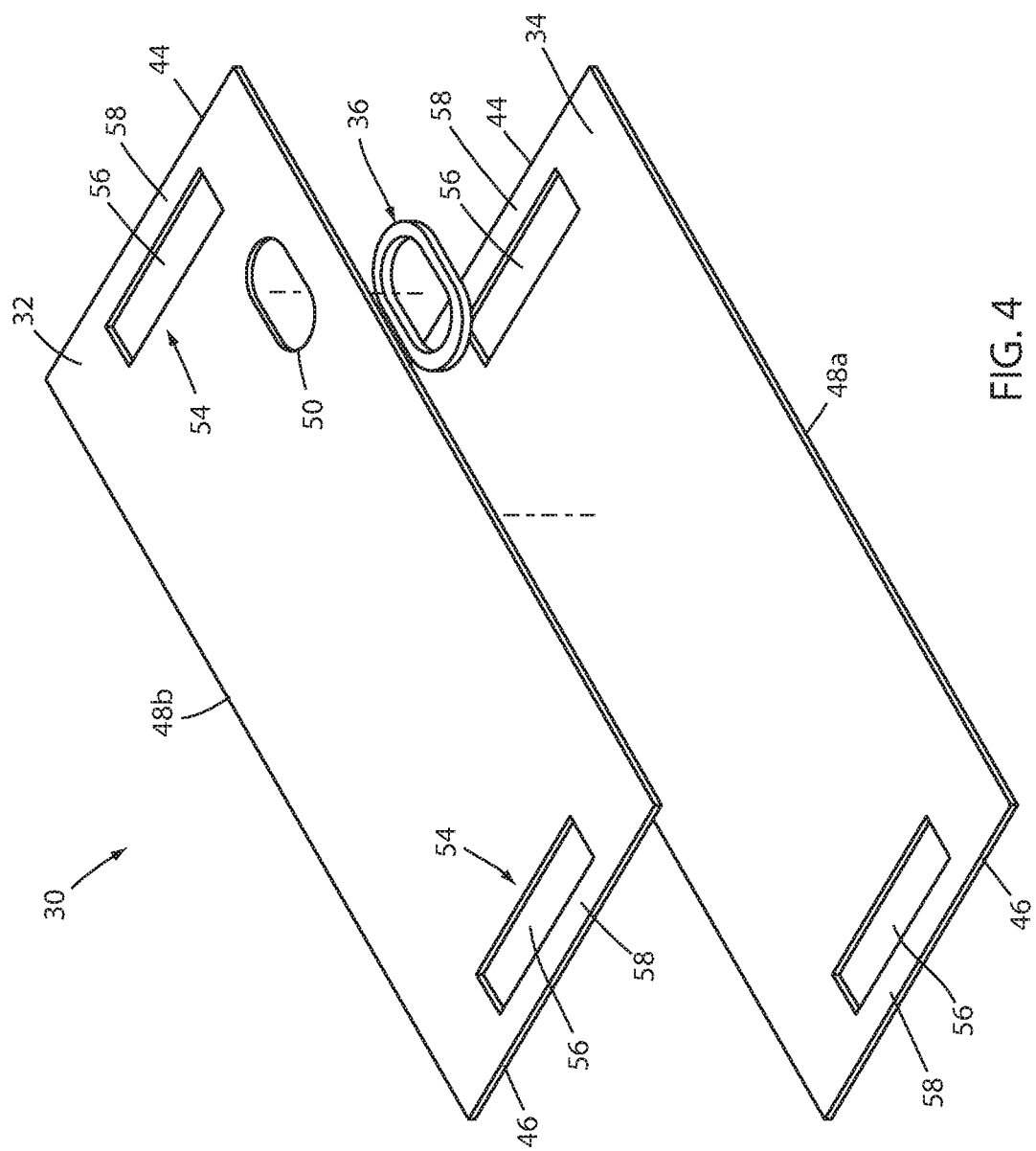
FIG. 4 is an exploded perspective view of the drainage bag of FIG. 2.

As shown more clearly in FIG. 4, drainage bag 30 includes an upper layer 32, a lower layer 34, and a float 36. Upper layer 32 is hermetically sealed to lower layer 34 along a perimeter seal 38 (FIG. 3). Upper layer 32 is also hermetically sealed to lower layer 34 along a plurality of handle seals 40. In at least one embodiment, each layer 32 and 34 is made from a flexible plastic material such as, but not limited to, a polyurethane, a polyvinyl chloride, or another type of thin-film, liquid-impermeable, flexible material. In some embodiments, perimeter seal 38 and handle seals 40 are constructed using one or more conventional thermoplastic welding techniques (ultrasonic welding, injection welding, laser welding, etc.), although other techniques may be used for sealing layers 32 and 34 together. In general, upper layer 32 and lower layer 34 are constructed of material that is flexible enough to expand in response to the atmospheric pressure exerted through opening 50 on the liquid therein, as will be discussed in greater detail below.

In the embodiment shown in FIGS. 3 and 4, drainage bag 30 includes a first end 44, a second end 46, and a pair of sides 48a and 48b. Drainage bag 30 is shaped as a rectangle in this example, but it will be understood that drainage bag 30 may take on different shapes, including but not limited to, a square or other polygon, a circle, an oval, or a non-polygon. Upper layer 32 includes an opening 50 defined therein. Opening 50 is positioned on upper layer 32 such that it will be aligned with a drainage port on the underside of thermal control unit 22 when drainage bag 30 is positioned underneath thermal control unit 22. In some embodiments, upper layer 32 includes printed markings, indicia, words, graphics, and/or other information thereon that facilitate aligning opening 50 with the drainage port without requiring the user to bend down and visually inspect the alignment of opening 50 with the drainage port. Such markings may include one or more lines intended to align with one or more edges, or other landmarks, on thermal control unit 22 when drainage bag 30 is properly positioned underneath thermal control unit 22. Such markings may also be located at other suitable locations.

Float 36 is secured to upper layer 32 (FIGS. 3 and 4). Float 36 may be secured to upper layer 32 in a variety of different manners. In one suitable embodiment, a top surface of float 36 is adhesively secured to an underside of upper layer 32. In an alternative embodiment, a bottom surface of float 36 is adhesively secured to the top side of upper layer 32. In still other embodiments, other techniques may be used to secure float 36 to upper layer 32.

Float 36 is constructed of a material that is buoyant in the liquid used with thermal control unit 22 such that, when the liquid is drained into drainage bag 30, float 36 floats in the liquid and thereby lifts up upper layer 32, as will be discussed in greater detail below. In some embodiments, float 36 is made of an open-celled foam, while in other embodiments, float 36 is made from a closed-cell foam. In still other embodiments, float 36 comprises one or more air pockets that are hermetically sealed. In at least one of the embodiments that includes a plurality of air pockets, float 36 is constructed of a conventional bubble-wrap type material adhered to upper layer 32. In another of such embodiments, upper layer 32 is constructed out of such a bubble-wrap type material and float 36 encompasses substantially the entire surface of upper layer 32. Still other constructions of float 36 are possible.

Figure 6:
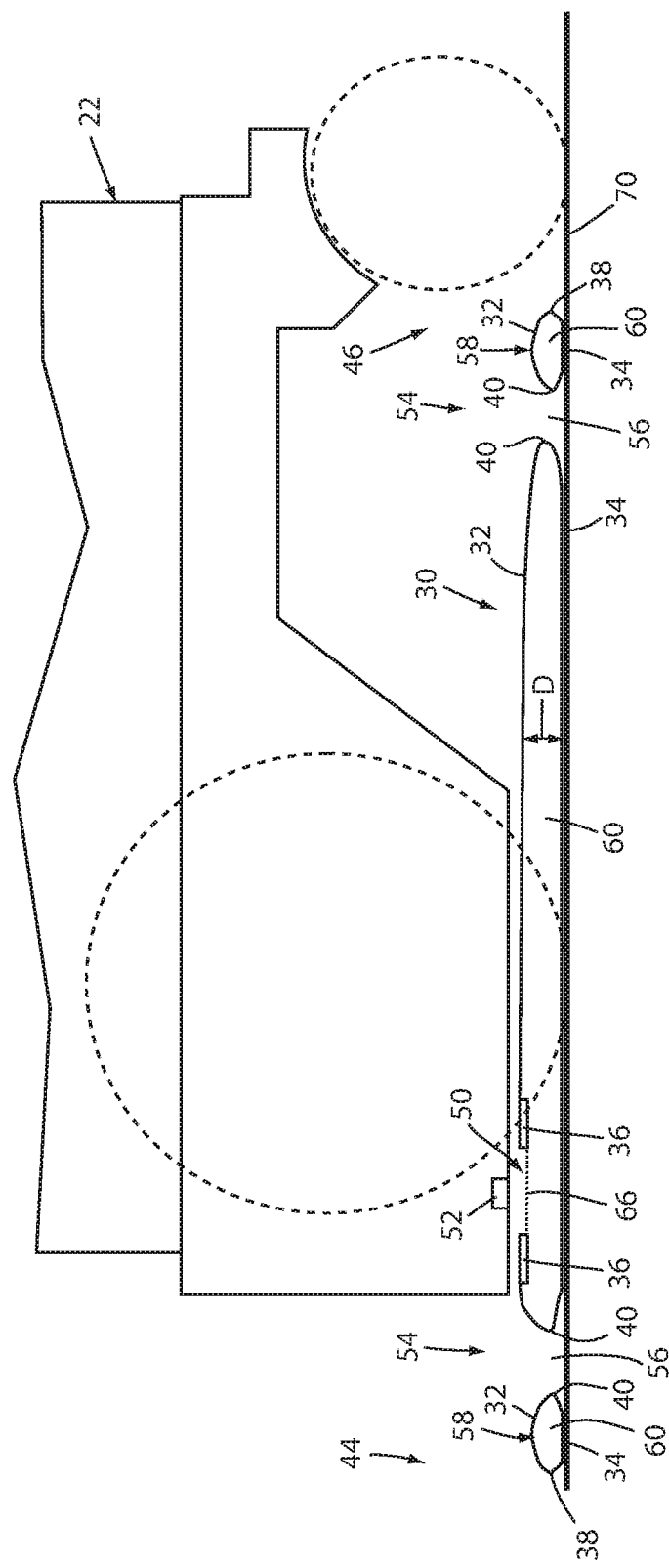
FIG. 6 is a side cross-sectional view similar to FIG. 5 showing the drainage bag after being filled with liquid from the thermal control unit.
Figure 7:
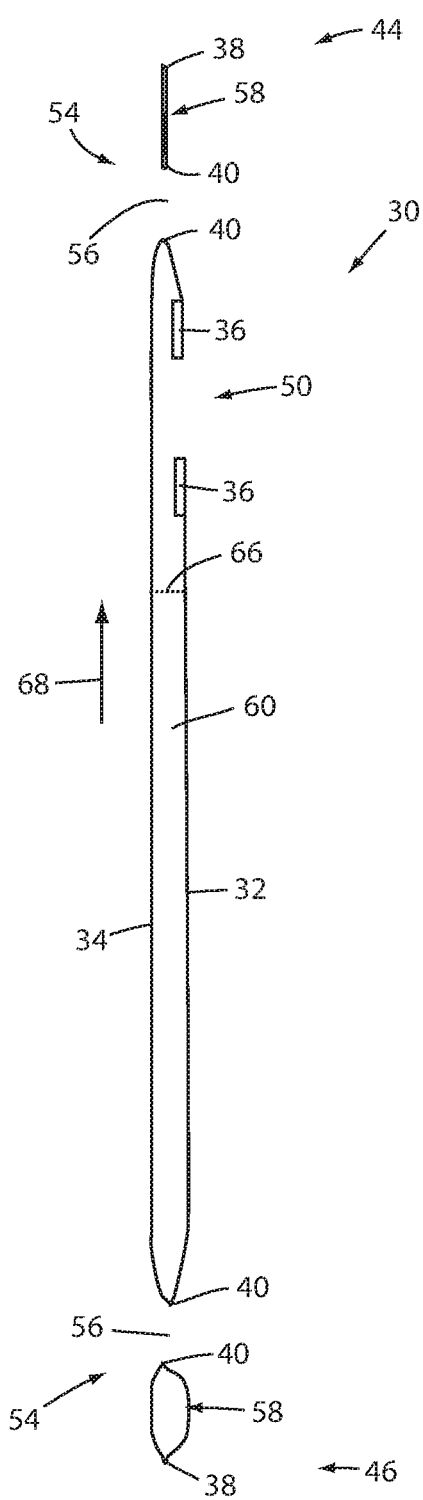
FIG. 7 is a side cross-sectional view of the filled drainage bag similar to FIG. 6 but shown in a generally vertical orientation.

Float 36 is constructed such that it lifts upper layer 32 in at least the region of opening 50 when liquid is present in bag 30. This helps ensure that upper layer 32 remains lifted above the liquid line 66 (see FIG. 6 or 7) at all times, thereby helping to ensure that the liquid does not flow over the opening 50 and onto a top surface of upper layer 32. The height of float may also be chosen to form a splash guard so that, as water impacts lower layer 34 after draining out of drainage port 52, any splash back that occurs as a result of the liquid's impact with bottom layer 34 generally does not have enough momentum to splash above the top of float 36, thereby retaining the liquid inside an interior space 60 (FIGS. 6 and 7).

It will be understood that various alterations to the design of float 36 may be made. For example, although FIGS. 3 and 4 depict float 36 as extending completely around opening 50, float 36 may be segmented and/or extend only partially around opening 50. Further, float 36 may include one or more channels for liquid to flow through, may be discontinuous, and/or may have different dimensions than what is shown in FIGS. 3 and 4.

Opening 50 is shown in FIGS. 3 and 4 as having an oval shape. It will be understood that this shape may vary, as well as the size of opening 50. In the illustrated embodiment, opening 50 has a substantially larger area than the area of the drainage port 52 (FIGS. 5 & 6) of thermal control unit 22. This larger area means that a user of drainage bag 30 does not need to position drainage bag 30 underneath thermal control unit 22 in one precise location for opening 50 to be aligned with drainage port 52. Instead, drainage bag 30 can be positioned at a variety of locations and yet still have opening 50 vertically aligned with drainage port 52 such that when liquid empties out of drainage port 52, it falls into opening 50.

Drainage bag 30 further includes a pair of handles 54. Handles 54 are each defined by a corresponding handle opening 56 and adjacent handle strip 58. Handle openings 56 are defined in both upper and lower layers 32 and 34. Handle strips 58 include the area between handle openings 56 and the adjacent perimeter seal 38. Although FIGS. 3 and 4 depict drainage bag 30 as having two handles 54, it will be understood that this number may be varied. In at least one embodiment, drainage bag 30 includes only a single handle 54 that is positioned adjacent the end 44 or 46 of drainage bag 30 that is closer to opening 50 (in the illustrated example, this refers to first end 44).

Figure 5:
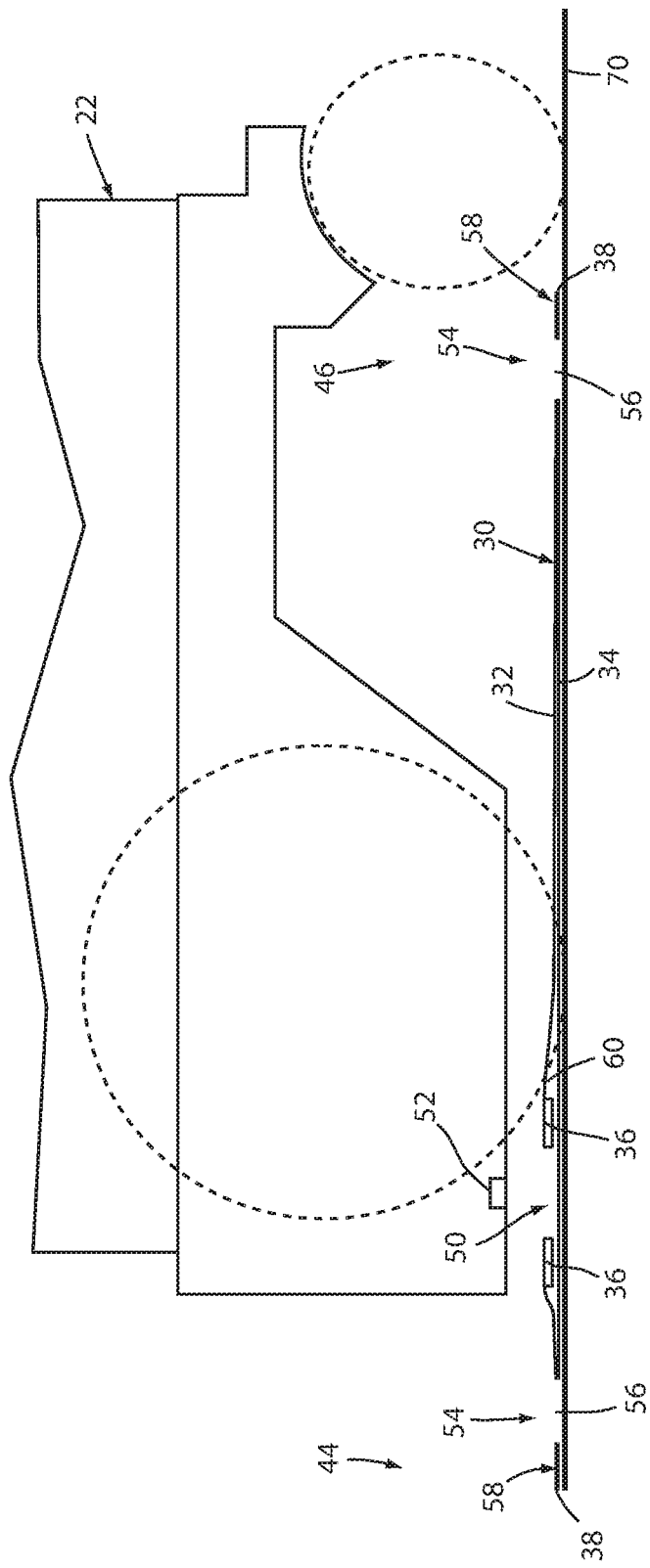
FIG. 5 is a cross-sectional view of the drainage bag taken along the line V-V of FIG. 3 and shown positioned underneath the thermal control unit of FIG. 2 with no liquid in it.

As shown more clearly in FIG. 6, drainage bag 30 includes an interior space 60 which is adapted to hold the liquid from thermal control unit 22. Interior space 60 is defined by upper layer 32, lower layer 34, and perimeter seal 38. Upper layer 32, lower layer 34, and perimeter seal 38 are all liquid impermeable such that liquid is only able to enter or leave interior space 60 via opening 50. When no liquid is present within interior space 60, drainage bag 30 assumes a generally flat and compact state, such as shown in FIG. 5. This enables drainage bag 30 to be stored in a compact manner. When drainage bag 30 is laid under a thermal control unit, such as thermal control unit 22, interior space 60 expands as liquid is drained into opening 50 (due to float 36), and continues to expand in order to accommodate the drained liquid.

In at least one embodiment, upper layer 32, lower layer 34, and perimeter seal 38 are dimensioned such that interior space 60 has a volume sufficient to receive all of the liquid within thermal control unit 22. In this manner, thermal control unit 22 can be entirely drained into a single drainage bag 30. This eliminates the need to partially drain unit 22 into drainage bag 30, lift and empty drainage bag 30, reposition drainage bag 30 back underneath thermal control unit 22, and then drain the rest of thermal control unit 22 into the emptied drainage bag 30.

FIG. 5 illustrates drainage bag 30 in an empty state while positioned underneath thermal control unit 22. When a user wishes to drain thermal control unit 22, he or she places drainage bag 30 in the position shown in FIG. 5. In this position, opening 50 of drainage bag 30 is vertically aligned with drainage port 52 (i.e. positioned underneath such that liquid draining out of port 52 falls into opening 50). After positioning drainage bag 30 underneath thermal control unit in this position, the user then opens a valve on thermal control unit 22 that allows fluid to flow out of drainage port 52. In the particular embodiment shown and described herein, thermal control unit 22 includes drainage port valve control 62 that is positioned underneath a reservoir 64 (FIG. 2). Valve control 62 is movable in a vertical direction. When it is pushed downward, drainage port 52 is closed. When it is lifted upward, drainage port 52 opens. By positioning valve control 62 underneath reservoir 64, the coupling of reservoir 64 to thermal control unit 22 automatically causes valve control 62 to be pushed downward, thereby sealing drainage port 52. This ensures that, whenever reservoir 64 is coupled to thermal control unit 22, the liquid inside does not flow into thermal control unit 22 and then proceed to directly exit via an open drainage port 52. Draining the liquid from the particular thermal control unit 22 shown in the attached drawings therefore requires that the user first remove reservoir 64 from the thermal control unit 22. It will be understood that thermal control unit 22 can be constructed in other manners that do not require the removal of a reservoir before draining the unit, as well as thermal control units that do not include a removable reservoir at all.

Once the user has lifted valve control 62 into its raised position such that drainage port 52 opens up, the liquid inside thermal control unit 22 begins exiting therefrom through drainage port 52. Gravity pulls the liquid downward and into opening 50 of drainage bag 30. The liquid falling into opening 50 begins to lift float 36 as the liquid begins to accumulate. The lifting of float 36 lifts upper layer 32 and thereby expands the volume of interior space 60. Float 36 continues to lift upper layer 32 higher and higher as more and more liquid enters interior space 60. This expands the volume of interior space 60 to match the volume of drained liquid. After all of the liquid has been drained from thermal control unit 22, drainage bag 30 looks similar to what is depicted in FIG. 6. That is, upper layer 32 is vertically spaced above lower layer 34 a distance D sufficient to accommodate the liquid received from thermal control unit 22.

After thermal control unit 22 has been drained, a user removes drainage bag 30 from underneath thermal control unit 22 by pulling on one of handles 54 in a generally horizontal direction. Once drainage bag 30 has been removed from underneath thermal control unit 22, the user is easily able to lift drainage bag 30 by grabbing one of handles 54. In order to avoid spilling the liquid within interior space 60, the user will typically wish to grab the handle 54 that is closer to opening 50 when lifting bag 30 into a vertical orientation. Such a generally vertical orientation is shown in FIG. 7 with arrow 68 pointing vertically upward.

When lifting drainage bag 30 into the generally vertical orientation of FIG. 7, gravity pulls the liquid downward toward the lower end of drainage bag 30, as indicated by liquid line 66. Drainage bag 30 is dimensioned so that liquid line 66 remains below opening 50, even when drainage bag 30 contains the full contents of thermal control unit 22. That is, opening 50 is offset from the center of drainage bag 30 and drainage bag 30 is dimensioned such that the portion of interior space 60 that lies below opening 50—when bag 30 is lifted into the vertical orientation of FIG. 7—has enough volume to receive all of the liquid from thermal control unit 22. By constructing drainage bag 30 in this manner, the user does not need to seal opening 50 when lifting drainage bag 30 to the vertical orientation of FIG. 7 and when carrying it to a sink, or other location, for disposal. In fact, in the illustrated embodiment, the user does not have to seal opening 50 at any time during the filling, transporting, and/or draining/disposal of drainage bag 30. Instead, by lifting drainage bag 30 using the handle 54 closest to opening 50, the liquid flows away from that handle 54 toward the opposite end 46 without spilling out of opening 50. It should be noted, however, that if a user were to lift drainage bag 30 while it was full using the handle 54 further from opening 50 (the handle adjacent second end 46 in the illustrated embodiment), the liquid would spill out of opening 50. In order to avoid that possibility, in some embodiments, the second handle 54 adjacent second end 46 is eliminated and drainage bag 30 includes only the single handle 54 adjacent first end 44.

It will be understood by those skilled in the art that, although FIGS. 5 and 6 illustrate drainage bag 30 positioned above a ground surface 70, this has been done merely for purposes of better illustrating the construction of drainage bag 30. In practice, lower layer 34 of drainage bag 30 rests on ground surface 70, which is generally a flat surface (e.g. the floor) upon which thermal control unit 22 is supported. Before liquid is drained into bag 30, upper layer 32 rests on top of, and in contact with, lower layer 34. In this unfilled state, interior space 60 has substantially zero volume due to the contact between upper layer 32 and bottom layer 34, which allows drainage bag 30 to be compactly stored. As liquid pours into opening 50, upper layer 32 rises due to the action of float 36 and the volume of interior space 60 increases.

It will be understood by those skilled in the art that a wide variety of different modifications can be made to drainage bag 30 beyond the several embodiments discussed so far herein. These include, for example, adding a seal and/or valve that fits over opening 50 so that when drainage bag 30 is not receiving liquid from thermal control unit 22, opening 50 is closed. In some such embodiments, the seal or valve is constructed such that after bag 30 is pulled out from underneath thermal control unit 22, but before being lifted, a user is able to manually close the valve or seal and thereafter lift bag 30 without the liquid being able to escape via opening 50.

As yet another alternative, thermal control unit 22 includes a magnetic material positioned around, or adjacent, drainage port 52 and drainage bag 30 includes a magnetic material disposed around, or adjacent, opening 50. When opening 50 is moved close to drainage port 52, the two magnetic materials attract and come into contact with each other, thereby ensuring that opening 50 is aligned with drainage port 52 and that the liquid exiting drainage port 52 does not flow outside of drainage bag 30. In some such embodiments, the magnetic material inside thermal control unit 22 is electromagnetic and user-activated and deactivated. In such embodiments, the user activates the electromagnet when positioning bag 30 under thermal control unit 22 and when draining the liquid thereinto. Once the liquid has drained into bag 30, the user may deactivate the electromagnet, thereby releasing its electromagnetic grip on drainage bag 30 and allowing a user to easily slide drainage bag 30 out from underneath thermal control unit 22 without requiring the user to manually exert a force sufficient to overcome the electromagnetic force between drainage bag 30 and thermal control unit 22. In still another embodiment, thermal control unit 22 includes a sensor for detecting the presence of drainage bag 30 (e.g. a Hall sensor, or the like, adapted to detect the magnet incorporated therein) and automatically activates its electromagnet. Thermal control unit 22 may further include a liquid level sensor that, when it detects the liquid has drained out of thermal control unit 22, sends a signal that causes the electromagnet to automatically deactivate.

In still another modified embodiment, drainage bag 30 may include a tube or channel coupled thereto that extends underneath thermal control unit 22 for alignment with drainage port 52. In such a modified embodiment, the main bag portion need not be inserted underneath thermal control unit 22, but instead only the tube or channel needs to be inserted thereunder. The tube or channel may include magnetic material on its end to magnetically couple to drainage port 52 to ensure contact is maintained therewith during draining. Still other modifications are possible.

In the embodiment illustrated herein, drainage bag 30 can be disposed of after a single use, or it can be re-used, if desired. Drainage bag 30 may also be modified to include a hydrophobic surface finish on the internally facing (e.g. facing interior space 60) sides of upper layer 32 and lower layer 34, as well as any portions of float 36 that may come into contact with liquid. Including such a finish helps resist any microbial growth or bacteria growth, and can therefore allow drainage bag 30 to be re-used multiple times without concern for any such growth spreading to thermal control unit 22. When drainage bag 30 is constructed in a manner in which it is intended to be re-used, the material of layers 32 and 32 may also be made thicker than when bag 30 is intended to be discarded after a single use. Still further, drainage bag 30 may be constructed to include a resealable opening adjacent one of ends 44, 46. The resealable opening is larger than opening 50 and is adapted to allow the user to more easily and/or more quickly drain bag 30 into a sink, or other disposal structure. In some embodiments, the resealable opening is positioned adjacent second end 46 such that the opening resides at the bottom of bag 30 when bag 30 is lifted into the vertical orientation of FIG. 7. The resealable opening may be constructed with one or more grooves and ridges that selectively interlock with each other in a zippered fashion, similar to a conventional ziplock style bag (e.g. a Ziploc® type of bag). Other types of resealing structure can also be used.

Still further, drainage bag 30 may be modified to include a degree of rigidity sufficient to allow it to be pushed underneath thermal control unit 22 without bunching, folding, or crumpling. When modified to include such a level of rigidity, a user can easily push the bag underneath thermal control unit 22 without concern that the bag is merely bunching up (which can lead to improper alignment between opening 50 and drainage port 52). In some situations, the rigidity is sufficient to allow a user to push bag 30 underneath thermal control unit 22 using his or her foot, thereby enabling the user to avoid having to bend down. When including such rigidity, upper layer 32 still maintains sufficient flexibility to allow float 36 to lift it upwards sufficiently to expand the volume of interior space 60 to receive the fluid from thermal control unit 22.

In some embodiments, the aforementioned rigidity of bag 30 is implemented by including a relatively stiff perimeter seal 38. In other embodiments, lower layer may be relatively stiff (e.g. stiff enough to be pushed under thermal control unit 22 without bunching). In still other embodiments, the rigidity may be accomplished through a combination of these or other techniques.

Figure 8:
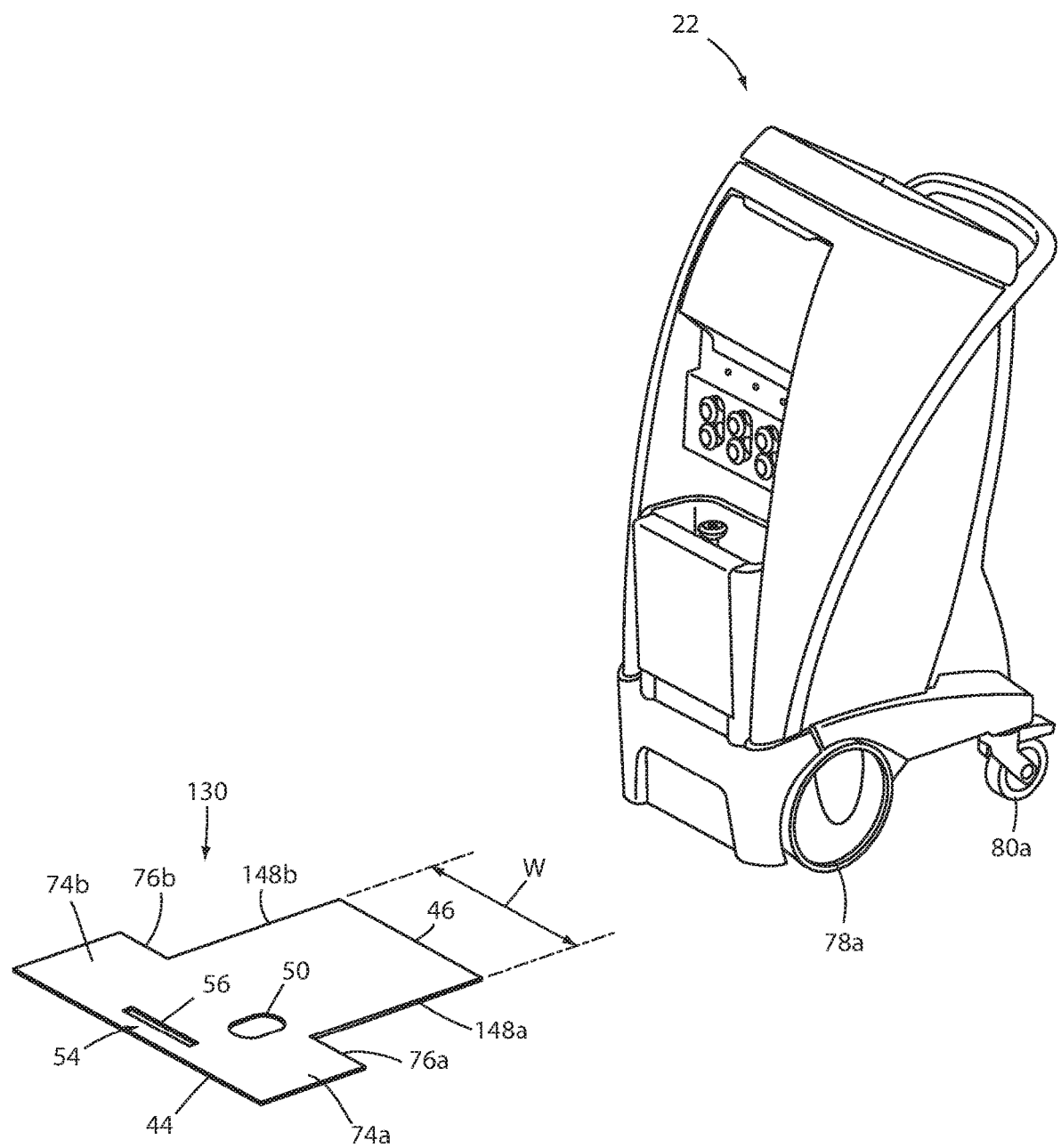
FIG. 8 is a perspective view of another drainage bag embodiment shown positioned in front of a thermal control unit.

FIG. 8 illustrates another embodiment of a drainage bag 130 according to the present disclosure. Those components of drainage bag 130 that are the same as drainage bag 30 are labeled with the same reference numbers and, unless otherwise noted, are not described further below. Those components of drainage bag 130 that are new are labeled with a new reference number. Those components of drainage bag 130 that are modified versions of similar components of drainage bag 30 are labeled with the same reference number increased by one hundred.

Figure 9:
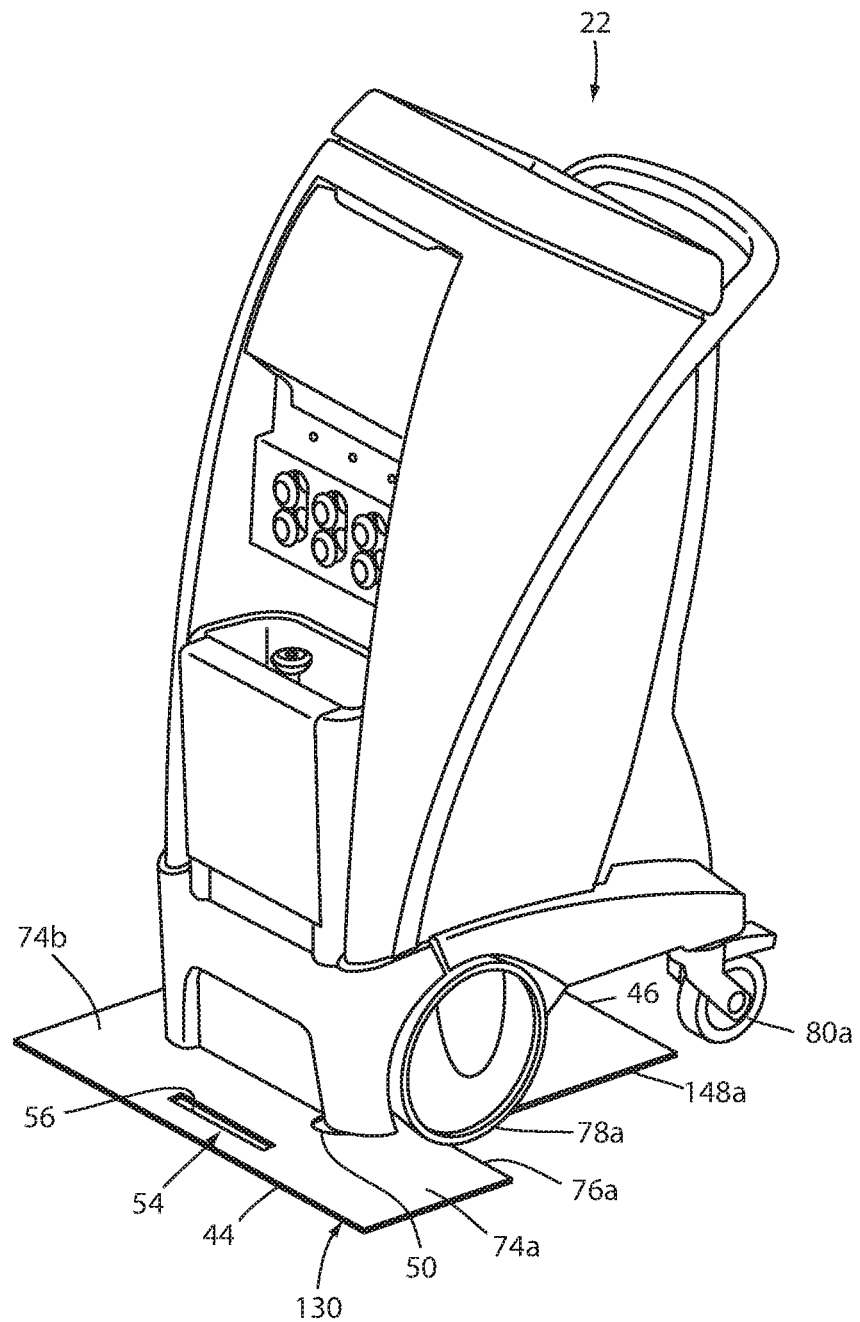
FIG. 9 is a perspective view of the drainage bag of FIG. 8 shown positioned underneath the thermal control unit.

Drainage bag 130 differs from drainage bag 30 in its shape. Drainage bag 130 includes a first or front end 44, a second or back end 46, and a pair of sides 148a and 148b. Sides 148a and 148b differ from sides 48a and 48b of drainage bag 30 in that they each include a shoulder 74a and 74b. Each shoulder 74a and 74b includes an abutment edge 76a, 76b. Abutment edges 76a and 76b are included in order to help facilitate proper alignment of bag 130 underneath thermal control unit 22. More specifically, drainage bag 130 is inserted underneath thermal control unit 22 until abutment edge 76a comes into contact with a first front wheel 78a of thermal control unit 22 and abutment edge 76b comes into contact with a second front wheel 78b of thermal control unit 22. (Note: second front wheel 78b is not visible in FIG. 8 or 9, but is shown in FIG. 2). FIG. 9 illustrates drainage bag 130 inserted underneath thermal control unit 22 with abutment edges 76 abutting against front wheels 78. When edges 76 are in this abutting position, opening 50 is aligned with drainage port 52 in the front-to-rear direction.

Drainage bag 130 also has a width W (the distance between sides 148a and 148b in the non-shoulder region, as shown in FIG. 8) that is almost as long as the entire lateral distance between front wheels 78a and 78b of thermal control unit 22. By having width W almost equal to the lateral distance between front wheels 78a, 78b, drainage bag 130 cannot be inserted underneath thermal control unit (without folding or bunching) in a manner wherein opening 50 is not laterally aligned with drainage port 52. Width W therefore helps ensure that a user can only insert drainage bag 130 underneath thermal control unit 22 in a position where opening 50 is laterally aligned with drainage port 52. Further, as noted above, abutment edges 76 help ensure that the user positions drainage bag 130 under thermal control unit 22 in a position wherein opening 50 is longitudinally aligned with drainage port 52. Drainage bag 130 therefore is easily positioned in proper alignment underneath thermal control unit 22 in a manner that does not require a user to bend down and/or visually confirm the vertical alignment between opening 50 and port 52.

Although not illustrated in FIG. 8 or 9, drainage bag 130 includes a float 36 and operates in the same manner as drainage bag 30. Further, although lower layer 34 of drainage bag 130 is not shown in FIG. 8 or 9 for reasons of visual clarity, drainage bag 130 includes both an upper layer 32 and a lower 34 that are secured together about a perimeter seal 38. In general, the construction of drainage bag 130 is the same as the construction of drainage bag 30 with the exception of shoulders 74 and abutment edges 76. Drainage bag 130 may also be modified in any one or more of the same manners drainage bag 30 may be modified, as discussed above. Such modifications include, but are not limited to, any one or more of the following features: incorporating antimicrobial coatings into bag 130, manufacturing bag 130 with a rigidity sufficient to allow it to be pushed underneath thermal control unit 22 without bunching (as opposed to requiring it to be pulled from one end), incorporating one or more magnet(s) into bag 130 to magnetically couple to the underside of thermal control unit 22, adding a valve or other structure for sealing and unsealing opening 50, etc.

Figure 10:
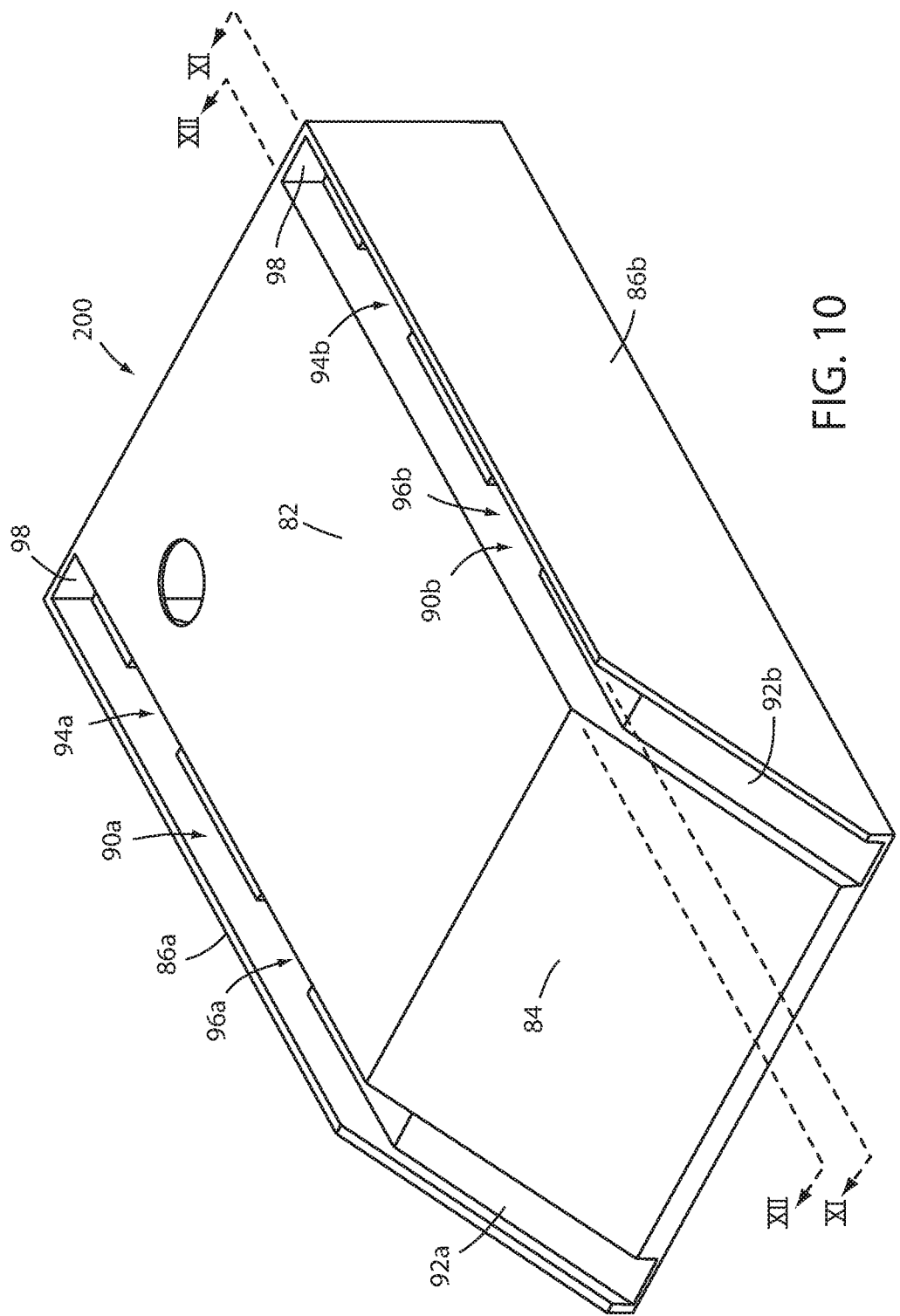
FIG. 10 is a perspective view of a drainage container according to another embodiment of the present disclosure.
Figure 11:
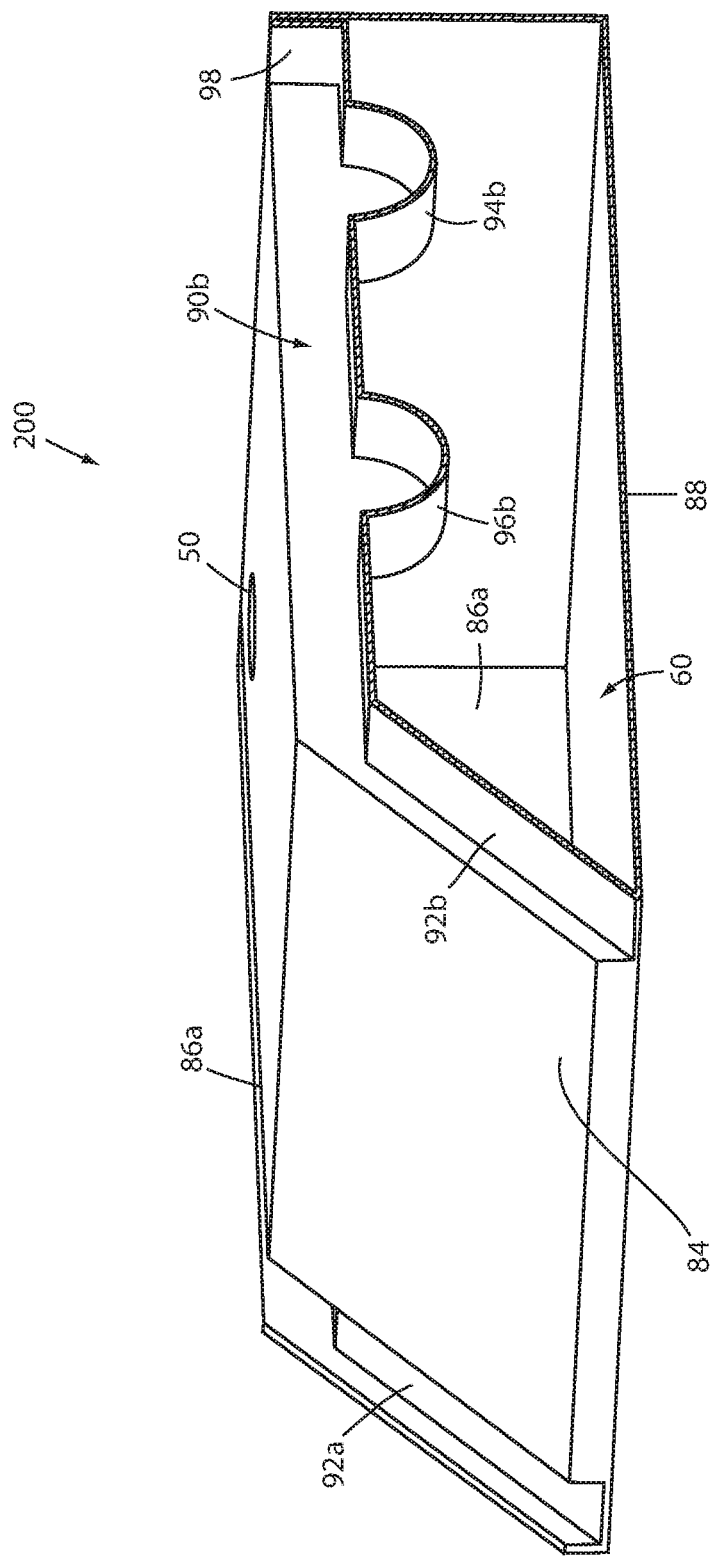
FIG. 11 is a perspective sectional view of the drainage container of FIG. 10 taken along the line XI-XI in FIG. 10.
Figure 12:
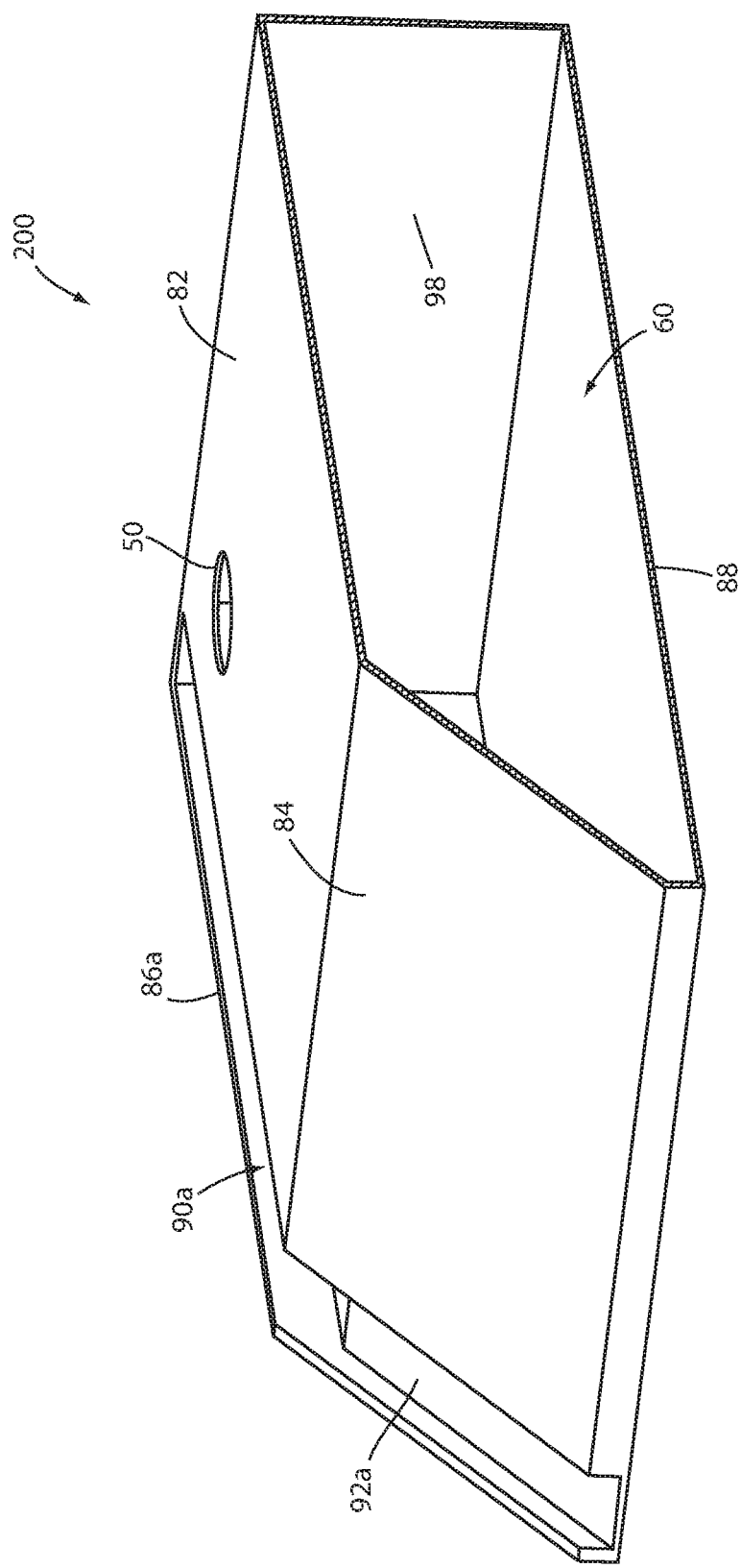
FIG. 12 is a perspective sectional view of the drainage container of FIG. 10 taken along the line XII-XII in FIG. 10.

FIGS. 10-12 illustrate a drainage container 200 according to another embodiment of the present disclosure. Drainage container 200, like drainage bags 30 and 130, is adapted to receive drained fluid from thermal control unit 22. Drainage container 200 includes several components that are the same as drainage bags 30 and/or 130 and are labeled with the same reference number. Those components that are new are labeled with a new reference number and those components that are modified include the same number increased by 200.

Drainage container 200 includes a top wall 82, front ramped wall 84, a pair of sidewalls 86a, 86b, a bottom wall 88 (FIGS. 11-12) and a pair of wheel channels 90a, 90b. Top wall 82 includes an opening 50 for receiving fluid from thermal control unit 22. Opening 50 opens into an interior space 60 (FIGS. 11-12) that is constructed to hold the liquid drained from thermal control unit 22. Interior space 60 possesses a volume sufficient to receive all of the liquid from thermal control unit 22. Interior space 60 is also constructed to be liquid impermeable (except for opening 50) such that liquid drained thereinto does not leak out of container 200.

Wheel channels 90 are adapted to receive front wheels 78 and rear wheels 80 of thermal control unit 22. More specifically, when thermal control unit 22 is to be drained, first front wheel 78a is rolled up a ramped surface 92a of first wheel channel 90a and second front wheel 78b is rolled up a ramped surface 92b of second wheel channel 90b. Thermal control unit 22 is then pushed forward until front wheels 78a and 78b are each nested in corresponding front wheel wells 94. If a user pushes thermal control unit 22 past front wheel wells 94, thermal control unit 22 is prevented from rolling off of container 200 by the contact of front wheels 78 with a rear wall 98 of container 200.

Once front wheels 78 of thermal control unit 22 are positioned in front wheel wells 94, thermal control unit 22 is positioned on top of container 200 such that opening 50 is aligned with drainage port 52. A user can then open drainage port 52 and allow the liquid to drain into interior space 60 of container 200. After the liquid has been drained from thermal control unit 22, unit 22 is wheeled back down ramped surfaces 92a and 92b and onto the ground. Container 200 may then be picked up and carried to a sink or other location for emptying its liquid contents. Container 200 may then be used again, or in some embodiments, disposed of.

Although FIGS. 10-12 depict front and rear wheel wells 94 and 96 having the same depth and dimensions, it will be understood that this may be modified so that the dimensions of front wheel wells 94 more closely match the dimensions of front wheels 78 and the rear wheel wells 96 more closely match the dimensions of rear wheels 80 of thermal control unit 22. Thus, if container 200 were to be used with the thermal control unit embodiment shown in FIGS. 8-9, in which front wheels 78 are larger than rear wheels 80, front wheel wells 94 will be deeper and accommodate a larger diameter wheel than rear wheel wells 96. Having front wheel wells 94 and rear wheel wells 96 dimensioned differently to match the wheels of thermal control unit 22 helps prevent a user from wheeling thermal control unit 22 backwards onto container 200, which would cause drainage port 52 to not be aligned with opening 50.

Container 200 is made of a rigid plastic material in at least one embodiment. Those portions of container 200 that define wheel channels 90 are made of a rigid material that is strong enough to support the weight of thermal control unit 22. Top surface 82, and/or any other surface not necessary to support the weight of thermal control unit 22, may be made of a non-rigid material, if desired.

Although not shown in the drawings, container 200 may also be modified to include any suitable features of drainage bags 30 and/or 130 described above. These features include any one or more of the following: incorporating antimicrobial coatings into the inside surfaces of those walls that define interior space 60 (thereby assisting in the re-use of container 200), adding a valve or other structure for sealing and unsealing opening 50, adding a handle to allow container 200 to be lifted (particularly from the end of container adjacent rear wall 98), etc.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A drainage bag for a thermal control unit adapted to deliver temperature-controlled liquid to a patient in order to control a temperature of the patient, the drainage bag comprising:
    a bottom layer;
    a top layer positioned on top of the bottom layer and sealed to the bottom layer about a perimeter, the top layer and bottom layer defining an interior space therebetween within the perimeter;
    an opening defined in the top layer; and
    a float adapted to lift a region of the top layer adjacent the opening as liquid from the thermal control unit is drained into the interior space from above the top and bottom layers, the float being constructed of a material that is buoyant in the liquid, and the float including at least one air pocket hermetically isolated from the interior space.

2. The drainage bag of claim 1 wherein the top layer is made of a flexible plastic and adapted to rest on top of the bottom layer when the interior space is empty of liquid.

3. The drainage bag of claim 2 wherein the bottom layer is made of flexible plastic.

4. The drainage bag of claim 1 wherein the float is constructed of the same flexible plastic as the top layer.

5. The drainage bag of claim 4 wherein the float includes a plurality of air pockets hermetically isolated from the interior space and the plurality of air pockets are distributed over and coupled to the top layer.

6. The drainage bag of claim 1 wherein the float is adapted to lift the top layer above the bottom layer such that a volume of the interior space expands enough to receive a volume of liquid in the interior space without the liquid spilling out of the interior space through the opening.

7. The drainage bag of claim 6 wherein the opening is defined in the top layer at a position offset from a center of the perimeter.

8. The drainage bag of claim 7 further comprising a handle coupled to the top and bottom layers, the handle adapted to allow a user to pull the drainage bag out from a generally horizontal orientation underneath the thermal control unit and to allow the user to lift the drainage bag to a generally vertical orientation.

9. The drainage bag of claim 8 wherein the position of the opening is defined in the top layer such that, when the drainage bag is lifted to the generally vertical orientation, a portion of the interior space is located below the opening such that the portion of the interior space is able to contain the volume of liquid.

10. The drainage bag of claim 8 wherein the opening remains open when the drainage bag is lifted to the generally vertical orientation.

11. The drainage bag of claim 1 wherein the top and bottom layers are both substantially planar when the interior space is empty of liquid.

* * * * *